United States Patent [19]

Ray et al.

[11] Patent Number: 5,762,643

[45] Date of Patent: Jun. 9, 1998

[54] VACUUM ASSISTED APPLICATION OF THIN VAPOR PERMEABLE, LIQUID IMPERMEABLE COATINGS ON APERTURED SUBSTRATES AND ARTICLES PRODUCED THEREFROM

[75] Inventors: Carl D. Ray; Paul E. Thomas, both of Terre Haute; Robert K. McBride, Jasonville; Peter I. Chang, Terre Haute, all of Ind.

[73] Assignee: Tredegar Industries, Inc., Richmond, Va.

[21] Appl. No.: 333,978

[22] Filed: Nov. 3, 1994

[51] Int. Cl.$^6$ .............................. A61F 13/15; B32B 3/10
[52] U.S. Cl. ..................... 604/383; 428/132; 428/138; 504/385.1
[58] Field of Search .............................. 604/383, 385.1; 156/199, 209, 459; 428/138, 132

[56] References Cited

U.S. PATENT DOCUMENTS

| | | |
|---|---|---|
| 3,881,489 | 5/1975 | Hartwell . |
| 3,929,135 | 12/1975 | Thompson . |
| 3,989,867 | 11/1976 | Sisson . |

(List continued on next page.)

FOREIGN PATENT DOCUMENTS

| | | |
|---|---|---|
| 057483 | 8/1982 | European Pat. Off. . |
| 057484 | 8/1982 | European Pat. Off. . |
| 066672 | 12/1982 | European Pat. Off. . |
| 141654 | 5/1985 | European Pat. Off. . |
| 203823 | 12/1986 | European Pat. Off. . |
| 227037 | 7/1987 | European Pat. Off. . |
| 305123 | 3/1989 | European Pat. Off. . |
| 502237 | 9/1992 | European Pat. Off. . |
| 538713 | 4/1993 | European Pat. Off. . |
| 2115702 | 9/1943 | United Kingdom . |
| 2175845 | 12/1986 | United Kingdom . |
| 2184389 | 6/1987 | United Kingdom . |
| 2184390 | 6/1987 | United Kingdom . |
| 2184391 | 6/1987 | United Kingdom . |

OTHER PUBLICATIONS

Abstract 110:9424p, Manufacture of Air–Permeable Propylene Polymer Films, hashimoto, Kuniji, Yamahara, Mitsuaki (Mitsubishi Petrochemical Co., Ltd.), Jpn. Kokai Tokkyo Kobo JP 63,117,043, May 21, 1988, Appl. 86/262,144, filed Nov. 4, 1996.

Abstract 110:40219r, Microporous Olefin Polymer Films, Ito, Tateoya, Tsuchn, Kutsuhiro, Yabe, Kenji (Toray Industries, Inc.), Jpn. Kokai Tokkyo Kobo JP 63,205,332, Aug. 24, 1988, Appl. 87/36,719, filed Feb. 19, 1987.

Abstract 106:51382r, Partially Porous Sheets, Naksmura, Shunichi Kuheko, Shinga (Tukuyang Soda Co., Ltd.), Jpn. Kokai Tokkyo Kobo JP 61,209,129, Sep. 17, 1986, Appl. 86/38,794, filed Mar. 1, 1985.

Abstract 106:5140jz, Porous Resin Films, Nagao, Kazotuka, Miki, Susumui Hamano, Keijiro (Okura, Industrial Co., Ltd.), Jpn. Kokai Tokkyo Kobo JP 61,230,922, Oct. 16, 1986, Appl. 86/73,177, filed Apr. 5, 1985.

(List continued on next page.)

Primary Examiner—John G. Weiss
Assistant Examiner—Dennis Ruhl
Attorney, Agent, or Firm—Emich, Schaffer, Schaub & Porcello, Co., L.P.A.

[57] ABSTRACT

A process for the manufacture of a vapor permeable, liquid impermeable composite material comprising a three-dimensional apertured substrate having a vapor permeable, liquid impermeable coating material thereon, the substantially liquid impervious composite material, and an apparatus for making the composite material are disclosed. Successive portions of a continuous sheet of an apertured substrate are passed into contact with a continuous moving perforated member. The coating material is supplied onto the substrate. The coated substrate is subjected to a vacuum which causes the coating material to flow onto the substrate material and in certain embodiments, at least partially into the apertures in the substrate. The vacuum is maintained for a period of time sufficient for the coating material to adhere to the substrate. The coated portions of the substrate are continuously removed from the moving member.

14 Claims, 5 Drawing Sheets

U.S. PATENT DOCUMENTS

| | | |
|---|---|---|
| 4,151,240 | 4/1979 | Lucas et al. . |
| 4,214,945 | 7/1980 | Lucas et al. . |
| 4,233,017 | 11/1980 | Lucas et al. . |
| 4,259,286 | 3/1981 | Louis et al. . |
| 4,272,473 | 6/1981 | Riemersma et al. . |
| 4,319,868 | 3/1982 | Riemersma et al. . |
| 4,321,924 | 3/1982 | Ahr . |
| 4,323,068 | 4/1982 | Aziz . |
| 4,323,069 | 4/1982 | Ahr et al. . |
| 4,324,246 | 4/1982 | Mullane et al. . |
| 4,324,247 | 4/1982 | Aziz . |
| 4,327,730 | 5/1982 | Sorensen . |
| 4,341,216 | 7/1982 | Obenour . |
| 4,341,217 | 7/1982 | Ferguson et al. . |
| 4,342,314 | 8/1982 | Radel et al. . |
| 4,347,844 | 9/1982 | Ohki et al. . |
| 4,364,723 | 12/1982 | Louis et al. . |
| 4,395,215 | 7/1983 | Bishop . |
| 4,404,241 | 9/1983 | Mueller et al. ............ 428/138 |
| 4,441,952 | 4/1984 | Mullane, Jr. . |
| 4,463,045 | 7/1984 | Ahr et al. . |
| 4,472,328 | 9/1984 | Sugimoto et al. . |
| 4,508,256 | 4/1985 | Radel et al. . |
| 4,509,908 | 4/1985 | Mullane, Jr. . |
| 4,552,709 | 11/1985 | Koger, II et al. . |
| 4,591,523 | 5/1986 | Thompson . |
| 4,601,868 | 7/1986 | Radel et al. . |
| 4,609,518 | 9/1986 | Curro et al. . |
| 4,617,085 | 10/1986 | Cole, Jr. et al. . |
| 4,626,252 | 12/1986 | Nishizawa et al. . |
| 4,629,643 | 12/1986 | Curro et al. . |
| 4,636,207 | 1/1987 | Buell . |
| 4,637,819 | 1/1987 | Ouellette et al. . |
| 4,681,793 | 7/1987 | Linman et al. ............ 428/138 |
| 4,695,422 | 9/1987 | Curro et al. . |
| 4,735,843 | 4/1988 | Noda . |
| 4,741,877 | 5/1988 | Mullane, Jr. . |
| 4,747,991 | 5/1988 | Bishop . |
| 4,772,444 | 9/1988 | Curro et al. . |
| 4,777,073 | 10/1988 | Sheth . |
| 4,778,644 | 10/1988 | Curro et al. . |
| 4,818,600 | 4/1989 | Braun et al. . |
| 4,839,216 | 6/1989 | Curro et al. . |
| 4,846,821 | 7/1989 | Lyons et al. . |
| 4,878,825 | 11/1989 | Mullane, Jr. . |
| 4,900,317 | 2/1990 | Buell . |
| 4,929,303 | 5/1990 | Sheth . |
| 4,950,264 | 8/1990 | Osborn, III . |
| 5,009,653 | 4/1991 | Osborn, III . |
| 5,055,338 | 10/1991 | Sheth et al. . |
| 5,085,654 | 2/1992 | Buell . |
| 5,158,819 | 10/1992 | Goodman, Jr. et al. . |
| 5,635,275 | 6/1997 | Biagioli et al. ............ 428/132 |
| 5,635,276 | 6/1997 | Biagioli et al. ............ 428/132 |

OTHER PUBLICATIONS

Abstract 106:51306a, Laser Etching of Polymer Films, Cole, Herbert S., Jr., Liu, Yung S., Phillipp, Herbert H. (General Electric Co.), U.S. Patent No. 4,617,085, Oct. 14, 1986, Appl. 771,956., Appl. 771,956, filed Sep. 3, 1985.

Abstract 106:6117g, Hydrophillic Porous Films or Sheets, Kumazaki, Shoji, Yamaguchi, Maasmi, Kashino, Minoru, Kamata, Hiroshi, Suzuki, You (Mitsubishi Chemical Industries Co., Ltd.), Jpn. Kokai Tokkyo Kobo JP 61,96,043, May 13, 1986, Appl. 84/216988, filed Oct. 16, 1984.

Nonwovens World (Feb. 1987), p. 63, Patent News.

Nonwovens Industry (Feb. 1989), Industry News, 1 pg.

Plastics World (Aug. 1994), New Briefs, p. 3.

Nonwovens World (1986), Breathable Absorbent Disposables—Market Developments and the Future, pp. 102–106.

Eastman Polyesters Plastics for Packaging ECDEL® Elastomers, pp. 1,22,23, May 1990.

VACUUM ASSISTED APPLICATION OF THIN VAPOR PERMEABLE, LIQUID IMPERMEABLE COATINGS ON APERTURED SUBSTRATES AND ARTICLES PRODUCED THEREFROM

TECHNICAL FIELD

The present invention relates to the application of a vapor permeable, liquid impermeable coating material onto an apertured three-dimensional substrate utilizing a vacuum coating process. In one aspect of the present invention thin layers of the coating material are applied to thin thermally sensitive apertured substrates. The present invention is especially useful in applying a coating material to microapertured polymeric webs such as those webs disclosed in the Goodman, Jr. et al., U.S. Pat. No. 5,158,819.

Readily envisioned uses for the present invention include a liquid impervious layer in such products as disposable absorbent articles including disposable garments for sanitary apparel purposes such as catamenial pads, diapers, incontinent articles, or for hospital pads, beds, surgical drapes, and for other products such as sleeping bag liners and the like.

BACKGROUND OF THE INVENTION

Absorptive articles such as diapers, catamenial products, surgical drapes and the like are designed to receive and retain liquid within an absorbent core. The absorbent article contains a cover or backsheet on the exterior of these articles which prevents the absorbed liquid from leaking or striking through the absorbent core. The liquidproof backsheet prevents self-drying of the absorptive article by any evaporation of the fluid held in the core material. The exterior liquidproof backsheet makes the absorptive article hot and clammy and ultimately uncomfortable to wear. Therefore, it would be an advantage to have a "breathable" material which permits exchange of vapors but retains fluids as a liquidproof backsheet.

One type of film, "breathable" film, is a "microporous" film wherein the micropores are interconnected through tortuous paths which extend from one exterior surface to the other exterior surface of the film. One method to create microporous film involves perforating the film by electrical discharge to form micropores. Other methods for making microporous films involve multi-step processing such as resin compounding, casting and forming the film, stretching, sintering and/or heatsetting or annealing of the film.

In various methods, the microporous film is formed by preparing and drawing a film containing at least one type of filler material. In various methods the filler is removed from the film while in other methods the filler is either allowed to remain intact within the film or is crushed under pressure to provide pores in the film.

The stretching step is critical in the formation of microporous films. In particular, many microporous films are produced by either uniaxially or biaxially stretching highly inorganic filled polymer films or by uniaxially or biaxially stretching the films made of immiscible polymer blends. The stretching causes open cell structures or interconnecting pores between the cells to form when the inorganic filler particles (or the incompatible polymer) separate from the polymer during the stretching process. Without undergoing the stretching process, the films are stiff and do not have micropores and are therefore not breathable.

Another type of microporous film is a unfilled polyolefin-base microporous film which is typically a weak film formed by blending polymer powders with a pore forming agent to form a slurry and thereafter blowing or die casting a single phase structure. The film is air or chill roll quenched to form a two phase film. The pore forming agent, such as mineral oil is partially miscible at extrusion temperatures but becomes immiscible at room temperature. The pore forming agent is then removed (by solvent extraction) to yield porosity in the film. Other films, while not using pore forming agents, are blends of polymers such as polypropylene and high density polyethylene which are drawn or stretched (such as cold rolling a crystalline film) thereafter hot stretching it until the pores are formed and then thereafter stabilizing by heatsetting. Still another method involves solvents wherein polyolefins are dissolved at elevated temperatures in a solvent which forms blocks or pockets of solvent-containing cells when the heated polymer is cooled down. The solvents are then removed from the pockets (micropores) in the polymer film.

In addition, non-polyolefin-based microporous films such as polytetrafluoroethylene and polyvinylidene difluoride microporous films are produced using a sintering and stretching process, or solvent process, respectively.

However, the microporous films prepared using these methods have several drawbacks. Many microporous films do not have sufficient water or liquid impermeability barrier properties and thus tend to leak.

Also, in microporous films the liquid barrier properties of the film depend upon phenomena related to the contact area and wettability of the film including the nature of the film surface. The barrier properties of the film are maintained only as long as liquid exhibits a high contact angle on the surface of the film. Once the liquid enters the pores the surface tension of the liquid and its contact angle on the walls of the pores in the film determine whether the pore structure will act as a barrier or as a sponge.

The microporous films are expensive to produce due to the extra resin compounding, stretching or orientation, and annealing steps which involve high capital outlay, conversion costs and equipment requirements. Further, the low line speeds and low production rates (the speed at which the film can be formed) add to the high cost. In addition, the formation of microporous films containing fillers requires a large quantity of organic filler in the resin blend which damages the film's physical properties, particularly the degree of maximum elongation of the film. Since the films have poor elongation properties, the films are easily torn. Further, the microporous films are not acceptably soft and are difficult to emboss due to the high filler content in the films.

As a result of intensive investigations to provide a vapor-permeable, liquid impermeable film or sheet which does not have the disadvantages of the above described microporous films or sheets, the present inventors have achieved the present invention. The present invention provides a monolithic (nonporous) film which is both vapor permeable and liquid impermeable and a method for making such film. For the first time, it is disclosed herein that a vacuum coating process can be used to form a multi-layer structure by coating a thin layer of a vapor permeable, liquid impermeable coating material onto a three-dimensional apertured film that has a three-dimensional embossed pattern on the film.

While an extrusion coating process has been used in the past to coat various substrate materials, until the present invention, no one had thought to extrude a vapor permeable, liquid impermeable material onto a film using a vacuum or pressure differential. The extrusion coating processes generally include an extruder slot (cast) die mounted in a position above a substrate to be coated. The substrate moves past the die and a molten stream of material is extruded onto the substrate. The thickness of the extrusion coating is controlled by the rate of output from the die and the rate of speed at which the substrate is moving beneath the die. The substrate can be moved beneath the stream of extrusion coating material flowing from the die in various ways. In certain methods the substrate is moved on a conveyor belt beneath the die. Other means include grabbing the substrate and moving it on driven rollers, beds or the like. Still other coating methods involve transporting the substrate over a roller or through a set of nip rollers adjacent the slot die. The coating material extrudes from the slot die onto the substrate at a point of interface at the nip. The nip rolls add pressure to the substrate and coating material at the interface to aid in achieving a bonding between the coating material and the substrate.

These extrusion methods require that the coating materials have a sufficient thickness such that the coating material completely coats the substrate and are no spaces or gaps in the coating material.

While it would be desirable to apply a vapor permeable, liquid impermeable coating to a substrate such as a three-dimensional apertured film, various difficulties occur when using the currently known coating technologies. Until the present invention, both the thermal energy or the extrusion coating systems and the compressive energy of the nip roll systems have made it virtually impossible to achieve good bonding (either chemical or mechanical) between the apertured substrate and any coating material applied thereto without causing damage to the apertures in the substrate itself. This is of particular concern when it is desired to apply a thin vapor permeable, liquid impermeable coating material to the apertured substrate.

Previous attempts to apply a coating material onto thin three-dimensional apertured materials which are particularly sensitive to excessive thermal loads have not met with success. The three-dimensional apertured material does not have sufficient mass to resist distortion under the required thermal load necessary to achieve a good bond between the extrusion coating material and the three-dimensional material.

It is therefore a primary object of the present invention to provide a vapor permeable, liquid impermeable three-dimensional film or sheet useful in disposable articles which is manufactured at low costs and to provide a process for the preparation of such film. The invention's added feature of vapor permeability provides even greater utility to a three-dimensional film.

It is therefore another object of the present invention to provide an improved method for applying a layer of a vapor permeable, liquid impermeable coating material to an apertured, three-dimensional film substrate.

It is still another object of the present invention to provide a vapor permeable, liquid impervious article comprising a vapor permeable, liquid impermeable coating material and a thermally sensitive three-dimensional substrate.

It is still another object of the present invention to provide a substantially liquid impervious article suitable for use in disposable articles such as diapers, incontinent pads, catamenial pads, surgical dressings, medical apparel and the like.

DISCLOSURE OF THE INVENTION

One aspect of the present invention relates to a method for applying a vapor permeable, liquid impermeable coating material to an apertured, three-dimensional substrate material and the coated substrate itself. According to the present invention, a vapor permeable, liquid impermeable coating material is extruded onto a top surface of an apertured substrate. A vacuum is applied to a bottom surface of the substrate as the coating material flows onto a portion of the substrate. It is to be understood that the three-dimensional apertured substrate has a planar side and a three-dimensional side and that the coating material can be applied either to the planar side or three-dimensional side of the apertured substrate. For ease of illustration herein, the side of the apertured substrate which receives the coating material will be identified herein as a "top" surface, while the opposite side of the apertured substrate which is adjacent the vacuum will be identified herein as a "bottom" surface. The vacuum pulls a fluid (such as air) through the apertures in the substrate. The vacuum pulls the coating material against the substrate and at least partially into the apertures in the substrate. The coated substrate is held under the vacuum pressure for a sufficient time to allow the coating material to adhere to the substrate and at least partially penetrate into the apertures. There is good bond strength between the substrate and the coating material without causing thermal distortion or damage to the apertured substrate. Good bond strength between the coating material and the substrate is achieved through adhesive bonding and/or mechanical bonding. According to the present invention a much thinner layer of the coating material can be applied to the substrate than was previously thought possible.

Another aspect of the present invention relates to a thermally sensitive apertured substrate coated with a thin layer of a vapor permeable, liquid impermeable coating material.

In a particularly preferred embodiment, the present invention comprises a composite multi-layer film having a three-dimensional film layer having multiple apertures which face outwardly and which come into contact with a wearer or user's skin. The composite multi-layer film further has an inner layer comprised of a substantially vapor permeable, liquid impermeable coating material which prevents any liquid material from penetrating or leaking through the liquid impervious coating material. The coating material layer is extruded onto the three-dimensional film layer using the method of the present invention.

Thus, composite films of the present invention provide highly desirable vapor permeable, liquid impermeable characteristics and also provide the advantage of the desirable tactile suede or cloth-like properties of the microapertured structures. The articles produced using the films of the present invention exhibit lower levels of noise when subjected to movement relative to a wearer's body. The composite article is sufficiently thin, soft and compliant and exhibits an attractive cloth-like tactile impression. Further, the composite film has good elongation rates and is sufficiently tough to withstand high strain rates when the films are rapidly elongated.

BEST MODE OF CARRYING OUT INVENTION

According to one aspect of the present invention monolithic films (i.e., non-microporous solid films) are coated onto a three-dimensional apertured substrate. The transmission of vapors and non-condensible gases occurs through activated diffusion through the monolithic films. The permanent gases or vapors, present on the side of the film having the highest concentration of gases or vapors, first dissolve in the surface of that side of the monolithic film. The gases or vapors diffuse across the film. Upon arriving at the opposite surface the gases or vapors desorb and enter the surrounding air space as a gas or vapor. The permeability is selective in monolithic films because permeability can be increased or decreased as the chemical and/or structural features of the polymers comprising the film are changed.

The liquid barrier properties of the film are provided by the density of the monolithic film which prevents the passage of condensed liquids regardless of the liquid's viscosity or surface tension. The liquid barrier properties are defined by burst strength, tensile properties or abrasion resistance of the film since no liquid flow is possible unless the film is ruptured. One advantage of coating monolithic films on a three-dimensional apertured substrate is that the monolithic films are free from any points of stress concentration, which points are created by the pores in a microporous film.

Another advantage is that the monolithic films are tough enough to withstand high strain rates of being rapidly elongated to at least about 400% elongation. In comparison, microporous films (especially films with high amounts of filler content) quickly shred under high strain rates. Still other advantages are that the monolithic films are water resistant, surfactant insensitive, have selective permeability, high water entry pressure, variable water swelling, good tear strength, absolute microbe barrier, and excellent odor barrier.

Various monolithic films which are suitable for use in the present invention and which can be extrusion coated onto a three-dimensional apertured substrate include polyethylenes (such as low density polyethylene) (LDPE), ethylene methyl acrylate (EMA) copolymers and ethylene vinyl acetate copolymers (EVA).

One type of monolithic film comprises a copolyester thermoplastic elastomer such as a copolyetherester elastomer having a randomized hard-soft segment structure which is permeable to polar molecules such as water but is resistant to penetration by non-polar hydrocarbons such as refrigerant gases.

Another type of monolithic film comprises thermoplastic polyurethane elastomers which are basically diisocynates and short chain diols (which form the basis of hard segments) and long chain diols (which form the basis of soft segments). Because the hard and soft segments are incompatible, the thermoplastic urethane elastomers exhibit two-phase structures which in turn cause the formation of domain microstructures.

Another type of monolithic film is a polyamide thermoplastic elastomer comprising hard and soft segments joined by amide linkages. These thermoplastic polyamide elastomers exhibit properties that depend upon the chemical composition of the hard (polyamide) and the soft (polyether, polyester or polyetherester) blocks as well as their segment lengths.

Still another type of monolithic film is a polymer/polymer composite combining polydimethyl siloxane and polytetrafluoroethylene (PTFE) in an interpenetrating polymer network; that is, the film is a physical blend of the two polymers rather than a copolymer or new compound.

Other useful coating materials include copolyesters which are very permeable to water vapor and impermeable to liquid water. One example of a suitable material is a copolyester of glycol (1,2-ethanediol) and a mixture of dicarboxylic acids made of the Eastman Company and is known as #14766.

In certain embodiments, specific useful coating materials can comprise high moisture vapor transmission rate grade thermoplastic elastomers such as the Eastman Company's ECDEL® copolyester; DuPont's Hytrel® copolyester; Ato Chem's PEBAX® polyamide copolymer; and Morton International and B. F. Goodrich's polyurethanes. In certain preferred embodiments, an ethylene methyl acrylate copolymer (EMA) an ethylene acrylic acid copolymer (EAA), an ethylene ethyl acrylate copolymer (EEA), an ethylene vinyl acetate copolymer (EVA) or an ethylene methacrylic acid copolymer (EMAA) can be blended with one or more thermoplastic elastomers to improve the draw down and extrudability of the thermoplastic elastomer into a thin coating to overcome any draw down difficulties due to the high elastic nature of the thermoplastic elastomer.

Another suitable coating material comprises a cold water resistant, hot water soluble polyvinyl alcohol coating. The cold water insoluble polyvinyl alcohol film has a high moisture vapor transmission rate and is a very clear and flexible film which is insoluble in cold water.

Still another suitable coating material comprises an alkaline soluble polymer which can be applied by extrusion coating onto a three-dimensional apertured film. The alkaline soluble coating layer is permeable to water vapor and impermeable to liquid water. The alcohol soluble coating layer insoluble in water at normal pH and is soluble in solution with high pH.

Still another suitable coating material comprises a water-repellant silicone or fluorine-type coating material which can be applied to the three-dimensional side of the apertured film. The water-repellant material changes the surface tension or contact angle of the water droplets on the film surface. The water-repellant material can be heat cured (i.e., crosslinked) or radiation cured (i.e., crosslinked by ultraviolet light and the like).

It is also within the contemplated scope of the present invention that other useful materials such as lubricants, surfactants, anti-blocking agents and the like can be used in the resin compound.

According to the process of the present invention, the coating material is applied to a three-dimensional apertured substrate. The three-dimensional apertured substrate has a smooth or planar side and a textured or three-dimensional side. In preferred embodiments the coating material is applied to the apertured substrate at a thickness of about 0.10 to about 1.0 mils and in certain embodiments, preferably about 0.20 to about 0.25 mils.

In certain preferred embodiments, the coating material is applied to the planar side of the three-dimensional apertured film; that is, the side of the film opposite side of the films having the three-dimensional structures forming the apertures. In other embodiments, the coating material can be applied to the three-dimensional side of the apertured substrate.

According to the process of the present invention the coating material is applied onto the three-dimensional film using a vacuum processing step which orients the coating material in a direction toward the three-dimensional apertured substrate rather than being oriented in the machine and/or transverse directions. That is, the coating material is oriented in the Z direction rather than in the machine and transverse (X and Y) directions. Thus, the present invention provides a vapor permeable, liquid impermeable film without the need for extra processing steps such as stretching, tentering, orienting or heat setting of the film.

In order to have the vapor permeable, liquid impermeable coating material adhere or bond to the three-dimensional apertured substrate, the coating material is supplied at a sufficiently elevated temperature at a point of interface. The interface is the point at which the two materials (the substrate and the coating material) come into contact with each other. The temperature of the coating material is sufficiently elevated so that there is sufficient thermal energy supplied at the point of interface. The elevated temperature causes at least one of the following: melting and fusing of both the coating material and the substrate together to form a bond, a chemical reaction of one with the other to form a bond, or melting and forming of the coating material on top of the substrate to form a cohesive and/or mechanical bond.

In situations where the substrate does not melt and fuse with the coating material, the presence of thermal energy at the interface is; no less important. The coating materials are designed to adhere to the substrates and are "thermally activated"; that is, no bonding will occur until the coating material has achieved a sufficiently elevated temperature. It is also desired that the coating material substantially cover the top surface of the substrate including the apertures in the substrate. It is desired that a maximum amount of surface area of the coating material is brought into contact with the substrate. The maximum amount of surface contact helps develop the bonding between the coating material and the substrate. It is to be understood that the cohesive bonding which occurs can be analogized to the phenomenon where a drop of oil is placed between two glass plates. When these plates are pressed together, the microscopic voids in the glass plates are filled by the oil and a form of suction exists. When one glass plate is lifted the other glass plate, which is cohesively bonded to the first glass plate, stays attached thereto.

It is important to understand that since the viscosity of fluids correlates to the temperature of the fluids, the higher the temperature, the less viscous the fluid. Therefore, maintaining a high temperature (i.e., low viscosity) as the coating material contacts the substrate is desired. This maintenance of thermal energy as, and after, the coating material contacts the substrate is controlled by two parameters of thermal dynamics, i.e., temperature and mass. The coating material is supplied at a sufficiently elevated temperature and at a sufficient mass in order to achieve a good bond. The substrate with the coating applied thereto is maintained at that sufficiently elevated temperature for a sufficient time for the bond to form without excessive distortion or damage to the substrate.

The polymers useful as vapor permeable, liquid impermeable coating materials, have well-defined upper limits of temperature which can be manipulated before degradation of the polymer occurs. The well-defined thermal degradation limit of the polymer necessarily controls the amount of heat supplied to the extrusion coating process. The remaining parameter which can be controlled is the mass of the coating material applied to the substrate. The mass is controlled by regulating the thickness of the coating material being applied to the substrate. In many end use applications, it is desired to apply as thin a layer of coating material as possible to the substrate. However, if too thin a coating layer is applied, the coating layer quickly loses heat and cools too quickly. Without sufficient heat, the low mass of coating material does not bond to the substrate. Therefore, the parameters of mass, temperature of the coating material, and the length of time at which the coating material and substrate are maintained at the proper temperature are controlled.

The thermal requirements of the extrusion coating process are further affected if the substrate itself is a thermally sensitive material. The amount of thermal energy applied to the thermally sensitive apertured substrate by the coating material is limited by the amount of thermal energy the substrate can tolerate without being damaged. The three-dimensional apertures which cause the resulting film material to have a cloth-like or silky tactile effect have open ends which are spaced apart from the plane of the film. The thickness of the film at these open ends thereof is further reduced. These thin open ends are especially sensitive to temperature and have the lowest mass point of the polymeric film and, as such, are the most critical to protect. It is important that the apertures not be crushed during the coating application of the vapor permeable, liquid impermeable material onto the apertured substrates. It is also important that the temperature and/or pressure applied during the application process not cause the ends of the apertures to melt and deform. When the apertures are melted or deformed, there is a less cloth-like tactile feeling to the coated film.

The coated substrate material has desirable low gloss and low modulus properties which indicate that the film has commercially acceptable softness and quiet or relatively noiseless properties. The coated substrate material thus exhibits lower levels of noise when subjected to movement by the end user.

Figure 1:
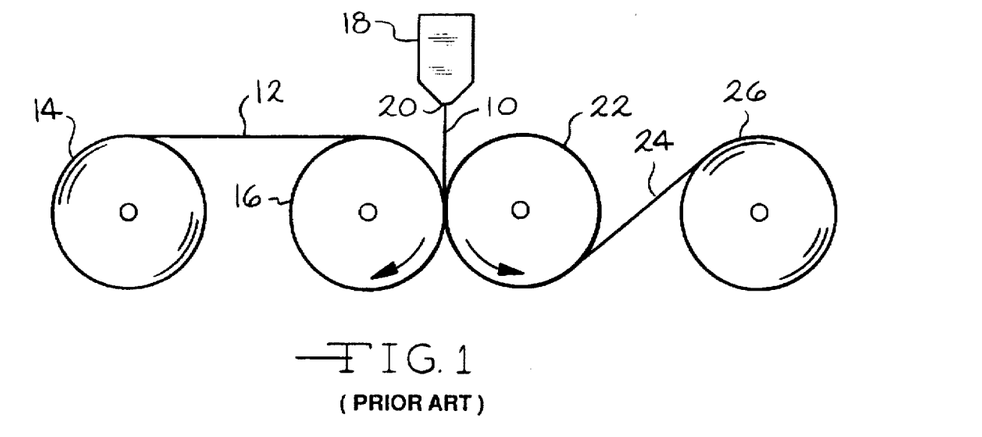
FIG. 1 is a simplified cross-sectional schematic illustration of a prior art process for coating a material onto a substrate.

Referring now to FIG. 1, a prior art method of applying a coating material 10 to a substrate 12 is generally shown. In the prior art embodiment shown, the substrate 12 is unwound from a roll 14 and passed over a roller 16. A nip roll 22 is present adjacent to the roller 16. A slot die 18 dispenses coating material 10 from an opening 20. Thereafter, a composite 24 which comprises the substrate 12 with the coating 10 adhered thereto can be wound up into a roll 26. In the extrusion process shown in FIG. 1, the coating material 10 is dispensed at a distance of approximately 1 to 3 feet above the nip defined by the roller 16 and the nip roll 22. Various problems with necking and beading of the coating material 10 occur at the nip as the coating material 10 is applied to a substrate 12. Therefore, the rate of speed at which the rollers 16 and 22 rotate is a limiting factor in applying an extrusion coating to a substrate 12. In addition, the coating material 10 generally must be delivered at a high temperature, generally about 550°–600° F., in order to have an adequate bonding between the substrate 12 and coating material 10. The coating only can be applied at thicknesses of about 0.5 mil and greater. This thickness or mass of the coating material is necessary in order to have sufficient heat transferred for a sufficient length of time in order to have bonding of the coating material to the substrate. Further, the nip pressure is needed to help bond the coating material to the surface.

Figure 2:
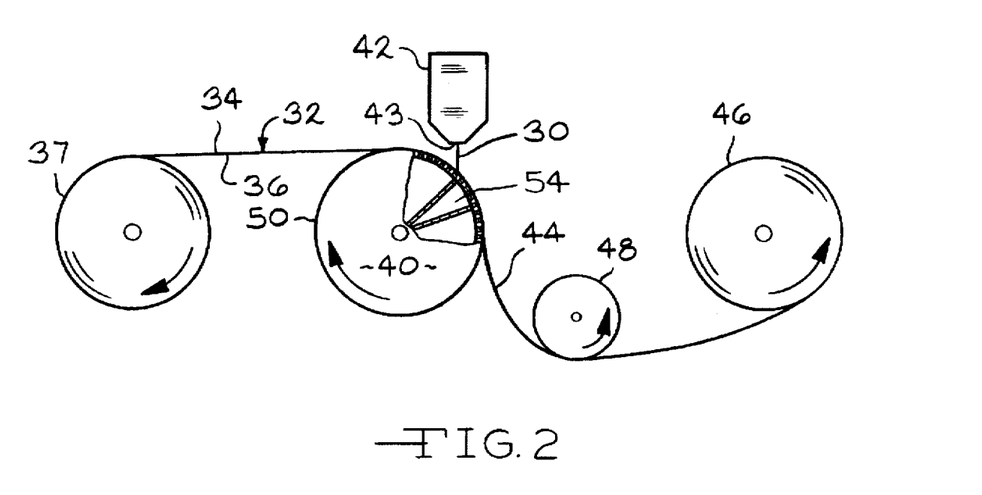
FIG. 2 is a simplified cross-sectional schematic illustration of a process for coating a material onto a substrate.
Figure 3:
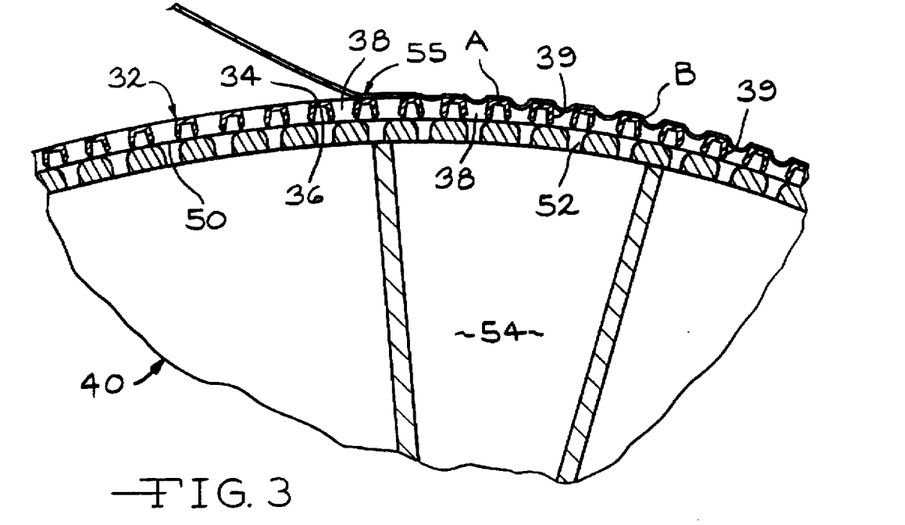
FIG. 3 is a simplified cross-sectional schematic illustration of a coating material being applied to a microapertured substrate.

One method of the present invention is generally shown in FIGS. 2 and 3. A vapor permeable, liquid impermeable coating material 30 is applied to an apertured substrate 32 having a top surface 34 and a bottom surface 36. In the embodiment shown in FIGS. 2 and 3, the top surface of the apertured substrate is planar while the bottom surface is three-dimensional. A plurality of apertures 38 each having at least one sidewall 39 extend through the substrate 32 and form the three-dimensional surface 36. In the embodiment shown the apertured substrate 32 is generally dispensed from a roll 38; however, it should be understood that the substrate 32 can be supplied by other means (not shown), including a film forming cast extrusion process.

The apertured substrate 32 passes over a substrate moving member or drum 40. It is to be understood that the moving member 40 can be a conveyor belt-type apparatus or other moving member 40, such as a drum. For ease of illustration, the substrate moving member 40 is depicted herein as a drum.

In the embodiment shown in the figures, the coating material 30 is initially formed by extrusion of a resin blend which is applied to the apertured substrate at an elevated temperature, such that the coating material substantially conforms to the top surface of the apertured substrate. Thus, while not shown in the figures herein, it is to be understood that, in other embodiments, the coating material can be supplied as a previously formed vapor permeable, liquid impermeable polymeric web or film which is heated to an elevated temperature, so as to cause the polymeric coated material to adhere to the substrate (e.g., melt, chemically bond or fuse onto the substrate) and then solidify on the substrate.

The coating material 30 is dispensed from a slot die 42 having an opening 43. In preferred embodiments of the present invention, the opening 43 is less than about 1 foot from the drum 40. In especially preferred embodiments, the opening 43 can be approximately 2 to about 5 inches, or more preferably approximately 2 to about 3 inches, from the top surface 34 of the substrate 32 as it passes over the drum 40. The coating material 30 is dispensed onto the substrate 32 to form a composite material 44 which is then wound on a roll 46. In certain embodiments, it is contemplated that at least one other roller 48 such as an idler roller and/or cooling roll can be utilized with the present invention. It is also within the contemplated scope of the present invention that the film can be subjected to other treatments including, for example, a corona treatment.

Referring now to FIG. 3 in particular, the drum 40 has a surface 50 which is highly perforated with a plurality of perforations 52 extending therethrough to allow a fluid such as air to pass through the perforations 52 in the surface 50 of the drum 40. When the moving member 40 is a drum, as shown in the figures herein, it is preferred that the surface 50 rotate at substantially the same rate of speed as the drum 40. A vacuum chamber 54, preferably located within the drum 40, is utilized to create a vacuum pressure between the top surface 34 and the bottom surface 36 of the substrate 32. As the coating material 30 is applied to the substrate 32 to form the composite material 44, the vacuum causes the coating material 30 to be pulled against the top surface 34 of the substrate 32. In certain embodiments, the coating material 30 is at least partially pulled into the apertures 38 of the substrate 32. The vacuum is sufficient to pull the coating material 30 against the top surface 34 of the substrate 32 while maintaining the integrity of the coating material 30. In preferred embodiments, the coating material 30 is applied to the top surface 34 of the substrate 30 at an interface point 55 just prior to applying the vacuum pressure to the substrate 30.

The vacuum pulls fluid, preferably air, which is present in the apertures 38 from the top surface 34 to the bottom surface 36 of the substrate 32. When the coating material 30 is applied to the substrate 32, the coating material 30 forms a barrier between the atmospheric pressure which would otherwise displace the air evacuated by the vacuum in the substrate 32. The removal of air from the apertures 38 causes the coating material 30 to be pulled against the top surface 34. The vacuum is applied such that sufficient pressure pulls the coating material 30 without perforating or tearing holes in the coating material 30.

The bond strength between the coating material 30 and the substrate 32 can be controlled by adjusting the vacuum pressure applied to the lower surface 36 of the substrate 32. A stronger vacuum pulls more coating material 30 into the apertures 38 and creates a stronger bond.

The coated substrate composite 44 is often subjected during use to peeling or shear forces. The bond strength between the coating material 30 and the substrate 32 is a factor in determining whether composite 44 will remain intact and not peel apart. The peeling forces are typically applied in a normal (90°) angle to any surface of the composite 44. According to certain embodiments of the present invention, the coating material 30 is at least partially pulled into the apertures 38 and at least partially coats the sidewalls 39 defining each aperture 38. The mechanical strength required to force the coating material 30 into apertures 38 provides an additional force (mechanical) which is beyond the thermal and adhesive forces already present between the substrate 32 and the coating material 30. Thus, it the adhesive force is in itself inadequate to provide the required bond strength, the additional mechanical force present in the composite 44 provides the additional bond strength to resist delamination or peeling.

Figure 4:
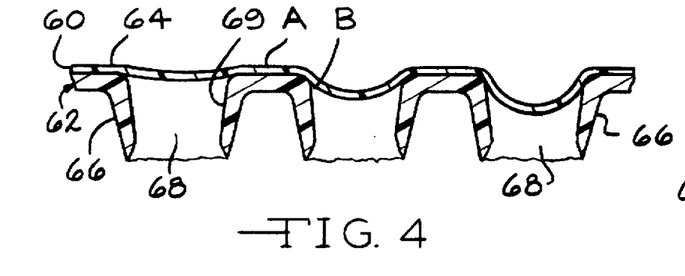
FIG. 4 is a simplified, greatly enlarged cross-sectional illustration of a coated three-dimensional substrate.

As shown in FIGS. 3 and 4, there is both an adhesive bond (A) and a mechanical bond (B) between the coating material 30 and the apertured substrate 32. The mechanical bonds (B) occur when the coating material 30 is pulled within the apertures 38 and at least partially conforms to the sidewalls 39 of the apertures 38.

According to the present invention, the coating material can be applied in layers as thin as about 0.10 to about 1.0 mils such that the composite material 44 does not have a "stiff" plastic feeling. Rather, the composite material is soft and has cloth-like tactile qualities. A further advantage is that a substantially thinner layer (and consequently, less amount) of coating material can be applied to the substrate. This decrease results in great cost savings. Also, a thinner layer is more permeable to vapors. Further, low cost coating materials such as polyethylene films and other examples, including polyethylene and other polymeric materials can be applied to the substrate.

Still another advantage is that according to the method of the present invention, it is possible to dispense the coating material 30 onto the substrate 32 at a point close to the point of interface 55 between the coating material 30 and the substrate 32. As seen in FIG. 2, it is possible to position the die 43 in a close adjacent relationship to the substrate 32. This close proximity between the coating material 30 and the substrate 32 means that it is possible to apply the coated material at lower temperatures than were previously possible. Since the time lapse between when the coating material 32 leaves the die 43 and when the coating material 32 is dispensed onto the substrate 30 is less than in prior art methods, the total heat flux is less. For example, in the case of applying polyethylene, previous extrusion methods required that polyethylene be extruded at temperatures between about 550°–600° F. at a distance of about 1–3 feet above the substrate. When polyethylene is coated onto a substrate, according to the method of the present invention, the polyethylene is extruded at a temperature of about 500° F. at a preferred distance of about 2–5 inches from the substrate. It has been found that when temperatures are decreased even by about 10° F., there is better application of the coating material onto the substrate. Further, in certain embodiments, the vacuum also cools the substrate and the coating material quickly as the coating material is pulled into or against the top surface of the substrate.

Figure 4A:
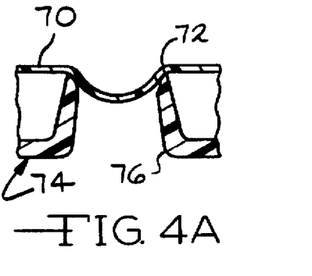
FIG. 4A is another simplified, greatly enlarged cross-sectional illustration of a coated three-dimensional substrate.

FIG. 4 shows one detailed embodiment wherein a vapor permeable, liquid impermeable coating material 60 is bonded to an apertured substrate 62. The apertured substrate 62 has a planar or top surface 64 and a three-dimensional or bottom surface 66. A plurality of apertures 68, each of which have at least one sidewall 69, extend from and define the three-dimensional surface 66. Mechanical bonds are formed at the areas "B", when the coating material 60 is applied adjacent the sidewalls 69 of the apertures 68. The coating material 60 conforms somewhat to the interior diameters of the apertures 68, such that there is less stiffness or rigidity to the coating material 60. FIG. 4A shows an alternative embodiment, wherein a coating material 70 is applied to a three-dimensional surface 72 of a film 74. The coating material 70 at least partially adheres to sidewalls 76 which define the three-dimensional surface 72.

Figure 5:
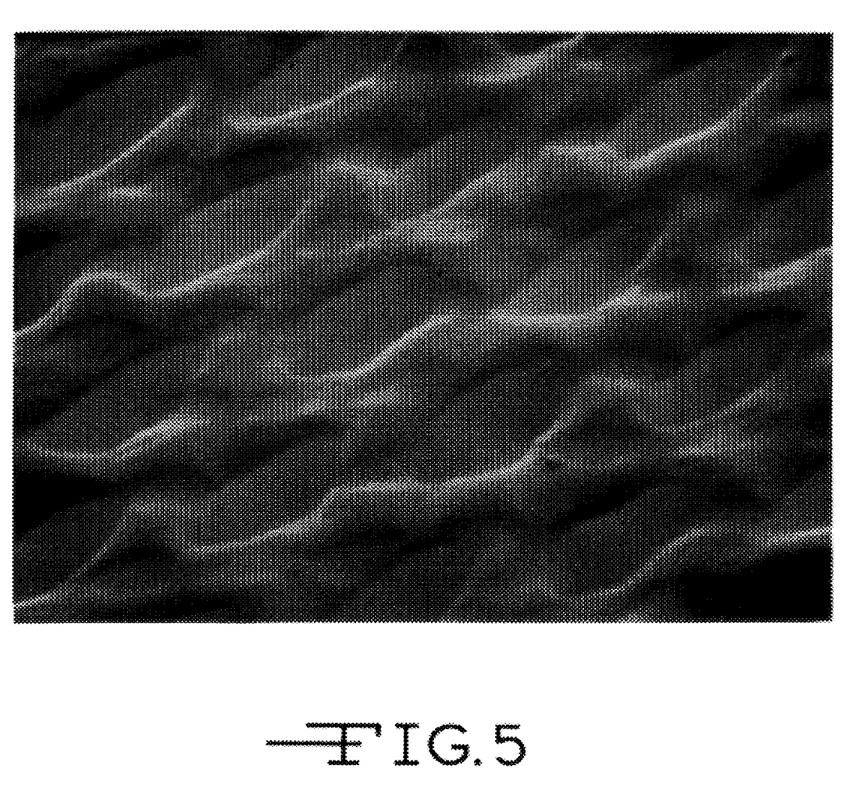
FIG. 5 is a scanning electron microphotograph (SEM) of a hydroformed three-dimensional film of 80 mesh as described in Example 1 herein and having a coating of about 0.25 mils showing the planar side at a 45° angle.
Figure 6:
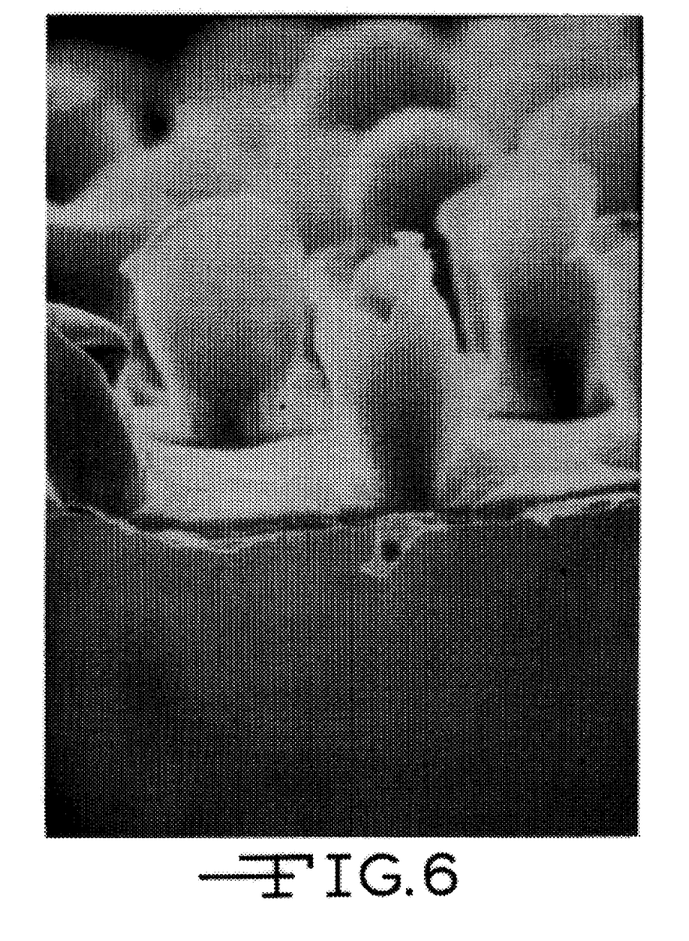
FIG. 6 is a SEM photograph showing a cross-sectional view of the film described in FIG. 5.

FIGS. 5 and 6 are scanning electron microphotographs of a three-dimensional apertured film coated with a vapor permeable, liquid impermeable material produced as described in Example 1 below.

It is to be understood that in various embodiments the breathable or vapor permeable films useful for various end uses require moisture vapor transmission rates preferably in the range of about 200 to about 4000 g/m²/day testing a 1 mil film tested at 100° F. and 90° relative humidity.

Figure 7:
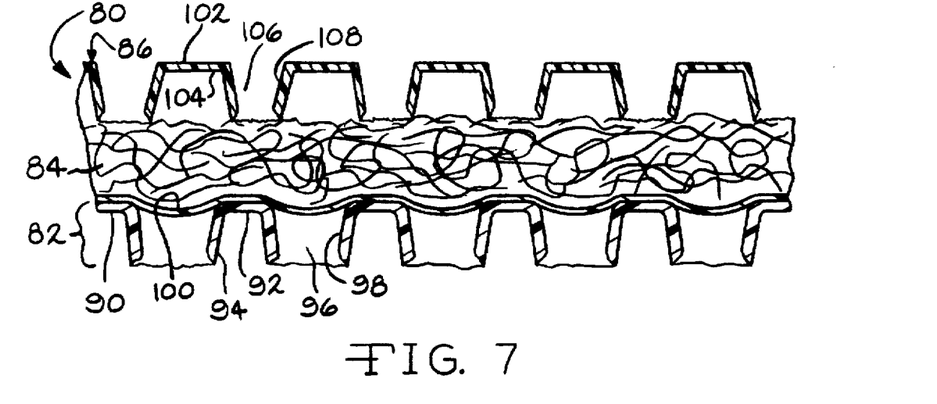
FIG. 7 is a simplified, greatly enlarged cross-sectional illustration of a coated microapertured substrate bonded to an absorbent pad and topsheet.

It is contemplated that various articles can be formulated using the film and method of the present invention. For example, FIG. 7 shows a section of a disposable product 80, generally comprising a vapor permeable, liquid impermeable coated substrate 82, an absorbent core 84, and a fluid pervious topsheet 86. The substrate 82 includes a three-dimensional apertured substrate 90 having a planar surface 92 and a three-dimensional surface 94. The three-dimensional surface 94 defines a plurality of apertures 96 each having sidewalls 98. The substrate 82 further includes a vapor permeable, liquid impermeable coating material 100 which is adjacent the planar surface 92 of the apertured substrate 90. The absorbent core 84 is placed between the coating material 100 of the substrate 82 and the fluid pervious topsheet 86. In the embodiment shown in FIG. 7, the fluid pervious topsheet 86 comprises a planar surface 102 and a three-dimensional surface 104 having a plurality of apertures 106, each of which are defined by sidewalls 108. It is; contemplated that at least one further layer such as a nonwoven layer (not shown) can be applied to the planar surface 102 of the fluid pervious topsheet 86.

Figure 8:
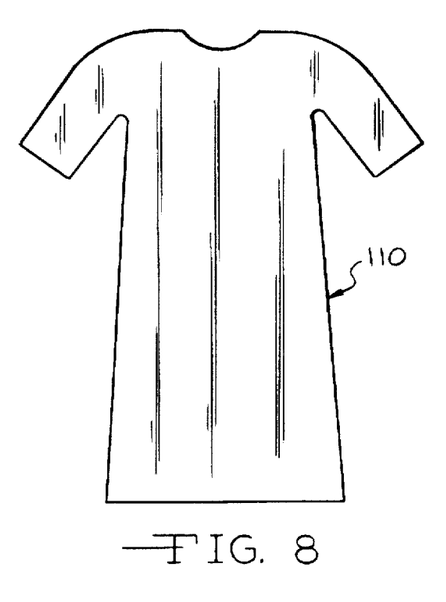
FIG. 8 is a simplified illustration of a protective gown using a vapor permeable, liquid impermeable coated three-dimensional apertured substrate.
Figure 9:
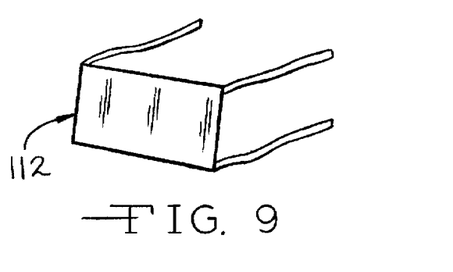
FIG. 9 is a simplified illustration of a facemask using a vapor permeable, liquid impermeable coated three-dimensional apertured substrate.
Figure 10:
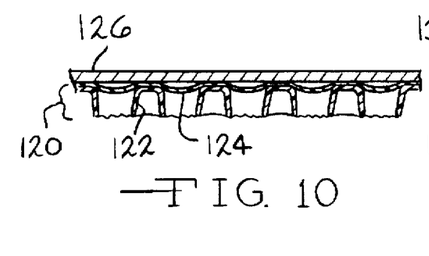
FIG. 10 is a simplified cross-sectional illustration of a multi-layer structure having a vapor permeable three-dimensional apertured substrate as at least one layer.
Figure 11:
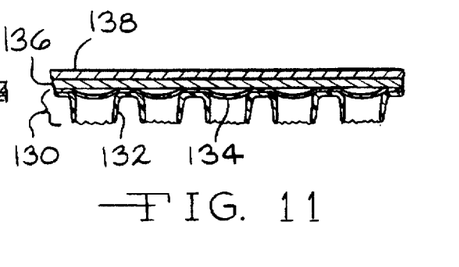
FIG. 11 is another simplified cross-sectional illustration of a multi-layer structure having a vapor permeable three-dimensional apertured substrate as at least one layer.

The vapor permeable, liquid impermeable three-dimensional film material is useful in providing a multi-layer breathable structure that has good resistance to penetration to fluids and, more particularly, liquids. The vapor permeable, liquid impermeable material is especially useful in applications where fluids are splashed or sprayed onto the breathable structure and the breathable structure provides resistance exposure to the fluid. This breathable structure can be utilized to great advantage in the medical fields, hazardous waste fields or other areas where people are interested in being protected from spilled or sprayed fluids. FIG. 8 shows a protective gown 110 and FIG. 9 shows a protective face mask 112 that can be made using a multi-layer breathable structure having the vapor permeable, liquid impermeable three-dimensional material as at least one layer. It is to be understood that breathable structures such as the structures shown in FIGS. 10 and 11, can further comprise at least one additional layer. FIG. 10 shows a vapor permeable, liquid impermeable three-dimensional material 120 comprising a three-dimensional film 122 and a vapor permeable, liquid impermeable coating material 124. It is to be understood that at least one layer 126 such as paper cover stock or nonwoven material that is lightweight and also highly breathable can be used with the vapor permeable, liquid impermeable three-dimensional material of the present invention. FIG. 11 shows a vapor permeable, liquid impermeable three-dimensional material 130 comprising a three-dimensional film 132 and a vapor permeable, liquid impermeable coating material 134. At least two layers 136 and 138 comprising, for example, absorbent or nonwoven materials and the like can be used with composite film of the present invention. It is further understood that the vapor permeable, liquid impermeable three-dimensional material can be present as an outermost layer, an intermediate layer or as an innermost layer in a multi-layer breathable structure. Those skilled in the art will readily recognize the advantages of positioning the vapor permeable, liquid impermeable material as such layers in order to take advantage of the desirable properties, including the moisture vapor transmission rate, toughness or durability, and aesthetic characteristics of the film.

Figure 12:
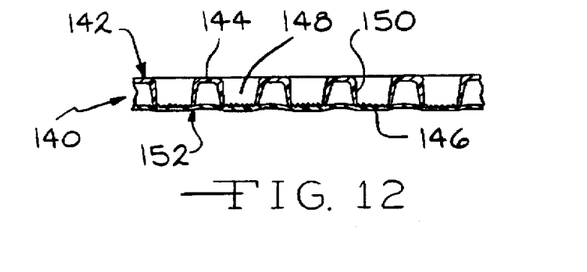
FIG. 12 is a simplified cross-sectional illustration of a multi-layer structure having a vapor permeable three-dimensional apertured substrate as at least one layer.

FIG. 12 shows a vapor permeable, liquid impermeable three-dimensional material 140 comprising a three-dimensional film 142 having a planar surface 144 and a three-dimensional surface 146. The three-dimensional surface 146 defines a plurality of apertures 148 each having sidewalls 150. A vapor permeable, liquid impermeable coating material 152 is applied to the three-dimensional side 146 of the film 142. This embodiment is especially preferred when the planar side of three-dimensional film has the desired tactile characteristics.

EXAMPLE 1

Pellets of a polyolefin (EMA copolymer, 80% of ethylene and 20% of ethylene methyl acrylate) were formed into a coating film 6.4 microns (0.25 mils) thick by extrusion from an extruder and die. Two inches below the slot die of the extruder was a rotating drum, as generally shown in Fig. 2. An 80 mesh pattern apertured formed polyethylene substrate was fed planar side up at 160 feet per minute to the rotating perforated drum under 5" Hg relative vacuum pressure which was sufficient to pull and bond the EMA coating material into the apertures of the 80 mesh polyethylene substrate. The resultant coated film has a moisture vapor transmission rate of about 334 g/m$^2$/day and is impervious to liquid water. The uncoated, three-dimensional surface has a soft cloth-like tactile impression.

EXAMPLE 2

Pellets of a non-polyolefin (Eastman copolyester #14766) were formed into a coating film 14 microns (0.55 mils) thick by extrusion from an extruder and die. Two inches below the slot die of the extruder was a rotating drum, as generally shown in FIG. 2. An 80 mesh apertured formed polyethylene substrate was fed planar side up at 22 feet per minute to the rotating perforated drum under 3" Hg relative vacuum pressure which was sufficient to pull and bond the coating material into the apertures of the 80 mesh polyethylene substrate. The resultant coated film has a moisture vapor transmission rate of about 992 g/m$^2$day and is impervious to liquid water. The uncoated, three-dimensional surface has a soft cloth-like tactile impression.

EXAMPLE 3

Pellets of an EMA copolymer (80% of ethylene and 20% of ethylene methyl acrylate) were formed into a coating film 8.5 microns thick by extrusion from an extruder and die. 3 inches below the slot die of the extruder molder was a rotating drum, as generally shown in FIG. 2. A patterned apertured (0.04" diameter holes, 35% open area) formed polyethylene substrate was fed three-dimensional side up at 126 feet per minute to rotating perforated drum under 2.5 inches Hg relative vacuum pressure which was sufficient to bond and pull the EMA coating material into the apertures of polyethylene substrate. The resultant coated film has a moisture vapor transmission rate of about 210.2 g/m$^2$/day and is impervious to liquid water. The uncoated planar surface has a soft cloth-like tactile impression.

It is to be understood that in other embodiments useful articles can be formulated having desirable moisture vapor transmission rates particularly suited to the end use needs required for that particular article.

Various other articles can be formulated using the method of the present invention. While particular embodiments of the present invention have been illustrated and described, it will be obvious to those skilled in the art that various changes and modifications can be made without parting from the spirit and scope of the invention and it is intended to cover in the claims herein all such modifications that are within the scope of this invention.

We claim:

1. A composite material comprising a vapor permeable, liquid impermeable coating material adhered to a three-dimensional apertured substrate having a planar side and a three-dimensional side, the three-dimensional side being defined by a plurality of apertures and sidewalls which extend from the planar side, each sidewall terminating at an open end, the coating material being substantially adhered to an area defined by the planar side or the three-dimensional side of the substrate without distortion or damage to the substrate, the coating material at least partially extending into the apertures in the three-dimensional apertured substrate, the coated three-dimensional substrate having a moisture vapor transmission rate of at least about 200 g/m$^2$/day at 100° F. and 90% relative humidity.

2. The composite material of claim 1, wherein the coating material comprises a monolithic, non-porous film.

3. The composite material of claim 1, wherein the coating material comprises an ethylene methyl acrylate copolymer.

4. The composite material of claim 1, wherein the coating material comprises low density polyethylene.

5. The composite material of claim 1, wherein the coating material is about 0.10 to about 1.0 mils in thickness.

6. The composite material of claim 1, wherein in the coating material is applied to the planar side of the substrate.

7. An article of protective clothing, comprising the composite material of claim 1.

8. The composite material of claim 1, wherein the coating material at least partially adheres to the sidewalls of the apertures.

9. An absorbent article comprising the composite material of claim 1, an absorbent core and a fluid pervious topsheet.

10. The absorbent article of claim 9, wherein the absorbent article is a disposable diaper.

11. The absorbent article of claim 9, wherein the absorbent article is an incontinent pad.

12. The absorbent article of claim 9, wherein the absorbent article is a catamenial product.

13. The absorbent article of claim 9, wherein the absorbent article is a surgical dressing.

14. A composite material comprising a vapor permeable, liquid impermeable coating material adhered to a three-dimensional apertured substrate having a planar side and a three-dimensional side, the three-dimensional side being defined by a plurality of apertures and sidewalls which extend from the planar side, each sidewall terminating at an open end, the coating material being substantially adhered to an area defined by the planar side or the three-dimensional side of the substrate without distortion or damage to the substrate, the coated three-dimensional substrate having a moisture vapor transmission rate of at least about 200 g/m$^2$/day at 100° F. and 90% relative humidity wherein the coating material is applied to the three-dimensional side of the substrate.

* * * * *